United States Patent [19]

de Castro et al.

[11] 4,415,655

[45] Nov. 15, 1983

[54] ELECTROPHORETIC SEPARATION OF ISOENZYMES UTILIZING A STABLE POLYACRYLAMIDE SYSTEM

[75] Inventors: Aurora F. de Castro, Union, Mich.; Surendra K. Gupta, Elkhart, Ind.

[73] Assignee: TechAmerica Group, Inc., Elwood, Kans.

[21] Appl. No.: 379,115

[22] Filed: May 17, 1982

[51] Int. Cl.$^3$ .................. C12Q 1/50; C12Q 1/32; C12N 9/04; C12N 9/12
[52] U.S. Cl. ........................................ 435/17; 435/26; 435/190; 435/194; 435/197; 435/814
[58] Field of Search ............... 435/17, 26, 190, 194, 435/197

[56] References Cited

U.S. PATENT DOCUMENTS 4,338,396 7/1982 Kiyasu .............................. 435/194

OTHER PUBLICATIONS

*J. Biochem.,* 71(3):543, (1972), H. Tamura & N. Ui, "A New Buffer System for Disc Electrophoresis . . . Proteins".
*Analytical Biochem.,* 78:459, (1977), M. Wyckoff et al., "Polyacrylamide Gel Electrophoresis . . . Procedure".
*Anal. Biochem.,* 20:246, (1967), A. A. Dietz et al., "Separation and Quantitation of Lactic . . . Electrophoresis".
*Clin. Chim. Acta.,* 21:151, (1968), T. D. Trainer et al., "A Rapid Method for the Analysis of Creatine . . . Isoenzymes".
"*Methods of Protein Separations,*" vol. 2, 1976, Table of Contents of Chapters 2 to 4.
*Clin. Biochem.,* 7:29, (1974), S. B. Rosalki, "Standardization of Isoenzyme Assays with Special Reference . . . Electrophoresis".
*Am. J. of Clin. Path.,* 43(3):256, (1965), J. A. Preston et al., "Rapid Electrophoretic Separation of Lactate . . . Acetate".
*Anal. Biochem.,* 63:241, (1975), K. Ariyoshi et al., "An Apparatus for Thin Layer Vertical . . . Gel System".
*J. Urology,* 118:204, (1977), J. T. Gayhack et al., "Lactate Dehydrogenase Isoenzymes in Human . . . Malignancy?".
*Anals of Clin. Lab. Sci.,* 4:456, (1974), D. J. Blomberg et al., "Isoenzymes of Creatine Kinase; Separation . . . Electrophoresis".

*Primary Examiner*—Lionel M. Shapiro

[57] ABSTRACT

A method for separating isoenzymes is disclosed. The method involves polyacrylamide gel electrophoresis in a buffer solution of a salt of 2-amino-2-methyl-1,3-propanediol at a pH of about 6.4 to 7.3 and an electrolyte buffer of 2-amino-2-methyl-1,3-propanediol taurine at a pH of about 8.0 to 10.0. After separation of the isoenzymes, the amount of individual isoenzymes present is determined.

7 Claims, No Drawings

ELECTROPHORETIC SEPARATION OF ISOENZYMES UTILIZING A STABLE POLYACRYLAMIDE SYSTEM

BACKGROUND OF THE INVENTION

Isoenzymes are multiple molecular forms of an enzyme derived from the same source and having at least one substrate in common. The multiple forms are sometimes tissue specific. They are generally separated by chromatography or electrophoresis. In the last decade, serum isoenzymes have become of particular interest due to their clinical significance in the evaluation and monitoring of the status of disease states.

Some examples of isoenzymes are: lactate dehydrogenase (LDH), creatine kinase (CK), glucose-6-(P)-dehydrogenase, alkaline phosphatase, acid phosphatase, amylase, δ-glutamyl transpeptidase (GGT), glutamateoxaloacetate transaminase (GOT), aspartate aminotransferase (AST), monoamine oxidase and acetylcholinesterase.

Lactate dehydrogenase (LDH) is an enzyme which is present in the human body in small amounts in the serum and tissue of healthy humans. LDH catalyzes the reversible reaction of pyruvic acid and lactic acid in the presence of nicotinamide adenine dinucleotide (NAD) as coenzyme. LDH consists of two different types of monomeric subunits, an H-type which is a heart (myocardial) type and an M-type which is a skeletal muscle type. The isoenzymes of LDH exist as five tetramer combinations which are designated $LDH_1$–$LDH_5$. These five tetramer combinations are made up of the M and H subunits combined as follows; $H_4$, $H_3M$, $H_2M_2$, $HM_3$, $M_4$, where $H_4$ corresponds to $LDH_1$, $H_3M$ to $LDH_2$, etc. LDH isolated from myocardial muscle, though catalyzing the same pyruvic acid reaction has a different isoenzyme pattern from that isolated from the skeletal muscle. In a healthy human the LDH isoenzymes are for the most part confined within the tissues. However, during abnormal growth of tissues to form tumors or in leukemia or other diseases such as hepatitis or during myocardial infarction, the LDH isoenzymes are found to be present in the serum in appreciable concentration.

Because the heart is a rich source of $LDH_1$, the demonstration of increased amounts in the serum is a valuable confirmation of the diagnosis of myocardial infarction. An increased $LDH_1$ content can often be detected as long as two weeks or more after the onset of symptoms. Similarly, in liver diseases an increase in the serum $LDH_5$ is found, especially in acute hepatitis, but also in more chronic conditions such as cirrhosis and obstructive jaundice, even when the total serum LDH activity is within the normal range. The determination of the level of LDH and the identity of the LDH isoenzymes therefore provides valuable information to the clinician in the diagnosis of various diseases.

Creatine kinase (CK, formerly designated creatine phosphokinase CPK) is an energy transfer enzyme which catalyzes the interconversion between adenosine triphosphate (ATP) and adenosine diphosphate (ADP) with the reversible phosphorylation of creation. Low levels of this enzyme are present in the human body. CK consists of two molecular subunits designated M and B. The dimeric structure of the enzymes results in three isoenzyme combinations: MM, MB and BB. CK-MM is found predominatly in the skeletal muscle and heart, CK-BB predominantly in the brain and smooth muscle, and CK-MB specifically in the heart. CK-MB is a specific and sensitive marker of myocardial necrosis. In addition, an elevated BB fraction has been recently found to have a high degree of correlation to some forms of cancer.

While CK-MB rises and falls quickly in the circulation after an infarct, $LDH-H_4$ ($LDH_1$) rises and falls at a slower rate. Because of this, CK-MB provides the fastest diagnosis to a myocardial infarct while $LDH-H_4$ can be a confirmatory test to a positive CK-MB or might be the only positive diagnostic signal if some time has elapsed after the infarct. Therefore, a commonly used approach for the assessment and documentation of cardiac injury is a combination of CK and LDH isoenzyme profile.

Because isoenzymes differ in several physiochemical properties, numerous separation procedures (chromatographic, immunochemical, electrophoretic) have been developed for their separation. Electrophoretic procedures have particularly been used.

In electrophoresis, charged molecules are propelled through a solid or semi-solid porous supporting medium by an electric field generated in an electrolyte which permeates the medium, the molecules are separated by their different electrophoretic mobilities. The supporting medium may be cellulose acetate, agarose or polyacrylamide.

The use of polyacrylamide gel in electrophoresis (PAGE) allows for a separation or fractionation of samples on the basis of molecular size in addition to the charge differences. The separation by size is the result of the sieving effect imparted by control of the gel pore size in a "separating gel" layer.

Oftentimes, the gels consist of two separately polymerized layers of polyacrylamide, the separating and the stacking gel. The polymer is the result of reaction between monomer and co-monomer or cross-linking agent (percent C). The sum of the concentrations of acrylamide monomer and cross-linking agent is expressed as percent T. The separating gel has a higher concentration of monomers and consequently a smaller pore size. The actual separation of the samples takes place in this gel. The restriction created by the small pores of this gel endows PAGE with high resolution power. There can be a second gel layer with larger pore size or stacking gel to help the sample concentrate itself into tightly-packed starting zones.

The gels are placed in an electrophoretic chamber containing electrolyte buffer. The sample, generally combined with a high-density solution and a tracking dye, is placed between the gel and the buffer. The high-density solution helps the sample diffuse less. The tracking dye helps to visually follow the progress of the electrophoresis and also functions as a reference point for the measurement of the relative mobility of the bands ($R_f$). Upon application of an electrical potential, the leading ion of the separating compartment, which is chosen to have a higher effective mobility than the sample species, migrates out in front of all others, while the trailing ion of the electrolyte buffer replaces it, both moving in the same direction. Behind the leading zone other zones form, depending on the specific mobilities of the sample species, and produce discrete bands. The buffer ions and pH are very critical to the good resolution of the macromolecular mixture to be separated and to the enzymatic activity remaining after the electrophoretic separation has occurred.

The present invention provides an improvement in acrylamide separation of isoenzymes, in particular LDH and CK.

DESCRIPTION OF THE PRIOR ART

Discontinuous (disc) electrophoresis utilizing polyacrylamide as the supporting medium has been claimed as one of the most effective methods for the separation of ionic components. As the name indicates, it employs discontinuous (multiphasic) buffers varying in chemical composition and properties on electrode wells and gels. The theory of discontinuous buffers was introduced by Ornstein and Davis [Ann. N.Y. Acad. Sci., 121:320 and 404 (1964)].

J. Biochem., 71:543 (1972) describes the use of a polyacrylamide gel with a buffer of 2-amino-2-methyl-1,3-propanediol chloride, designated "ammediol" chloride, at a pH of 9.5 in combination with ammediol glycine pH 8.8 electrolyte buffer for the purification of whole thyroid stimulating hormone (TSH). Analytical Biochem., 78:459 (1977) describes a similar ammediol chloride-ammediol glycine system containing sodium dodecyl sulphate (SDS) for the separation of some proteins. The pH range prior to electrophoresis was not described. The operating pH range used seemed between neutral to alkaline.

Discontinuous polyacrylamide gel electrophoresis of LDH isoenzymes using various buffers has been widely studied. For example, Anal. Biochem., 20:246 (1967); Anal. Biochem., 63:241 (1975) and J. Urology, 118:204 (1977) disclose electrophoresis of LDH isoenzymes using polyacrylamide gel and a tris (hydroxymethyl) aminomethane chloride ("tris") buffer at a pH of from 8.3 to 9.3 and a "tris"-glycine electrolyte buffer at a pH of 8.3.

Anals of Clin. Lab. Sci., 4:456 (1974) describes a tris-glycine system at a pH of 8.5 to 9.2 for the separation of CK isoenzymes.

National Technical Information Service, Springfield, Va. 22151, has available PB No. 196090 entitled "Multiphasic Buffer Systems Output" which is a computerized print-out listing over four thousand buffer systems. Among the compositions disclosed is a system of buffers containing ammediol, chloride ions, taurine and bicine ions. The pH range is indicated as being 7.5 to 10.6; a preferred pH is 9.2

To produce commercial polyacrylamide gels, it is desirable to produce stable gels with long shelf life. These gels then provide convenience to the user while making it possible to produce large numbers. The gels of the electrophoresis systems described above generally suffer from the following disadvantages At basic pH's the polyacrylamide gels are unstable soon after preparation, usually one week. Therefore the gels have to be prepared when the samples arrive to be tested for isoenzyme determination, either LDH or CK or other. In addition, when the enzymatic reaction for visualization of the LDH isoenzymes takes place using such gels, residual color background shows up between the bands which makes the determination of the amount of the individual isoenzyme present difficult to determine. Further, after the freshly prepared gels sit for about 24 hours before use, upon use the bands corresponding to LDH$_5$ fade considerably, affecting the comparative results obtained on day one of gel preparation with results of subsequent days. Furthermore, it is desirable to expedite the results, to have a system in which one can run at the same time (in the same vessel) both LDH and CK isoenzymes. There is a need for a convenient electrophoretic system and stabilized gel for the separation of isoenzymes to allow more precise separation and measurement of the individual isoenzymes.

SUMMARY OF THE INVENTION

The present invention is directed to an improved method for separation of isoenzymes. The method involves the steps of placing a sample on a support medium of polyacrylamide gel containing acrylamide monomers in a buffer solution of a salt of 2-amino-2-methyl-1,3-propanediol at pH of about 6.4 to 7.3. The gel support medium is placed in contact with an electrolyte buffer solution of 2-amino-2-methyl-1,3-propanediol taurine at a pH of about 8.0 to 10.0. The sample is subjected to a differential electrical potential to produce migration of the ions and isoenzymes present. After separation of the isoenzymes, the gels are removed and stained to produce well-defined isoenzyme bands. The amount of individual isoenzymes present can be quantitatively determined, e.g., by measuring the bands in a densitometer.

DETAILED DESCRIPTION OF THE INVENTION

As indicated earlier, a discontinuous PAGE system may have two separately polymerized layers of acrylamide gel, the separating gel and the stacking gel. Alternatively, the system can consist of only one gel, the separating gel.

The separating gel was prepared by the following method. Commercially available acrylamide, in solvent-recrystallized form, or recrystallized from acetone [See Methods of Protein Separation, Vol. 2, (1976)] was mixed with a cross-linking agent such as N,N'-methylenebisacrylamide ("Bis") or N,N'-diallyltardiamide; a free radical catalyst activator, such as potassium persulfate or riboflavin and N,N,N',N'-tetramethylethylenediamine and the gel buffer used in the present invention, 2-amino-2-methyl-1,3-propanediol.

Adjustment of the pH of the gel buffer to the range 6.4 to 7.3 has been found to be a critical limitation. The 2-amino-2-methyl-1,3-propanediol salt is prepared by the addition of an acid, e.g., hydrochloric, sulfuric, nitric, or hydrofluoric acid to the propanediol compound. Propanediol salts of chloride and sulfate are preferred. This forms a salt solution which can be adjusted to a pH of about 6.4 to 7.3. If the pH of the buffer is much above 7.3, or below 6.4, the acrylamide gel is unstable soon after being prepared and deteriorates so as to be unusable in electrophoresis and the isoenzyme bands are not clearly resolved. In a preferred embodiment of the invention, the polyacrylamide gel is prepared in a gel buffer of pH 6.7 to 7.1.

A useful range of acrylamide monomer concentration is from about ½ to 30 percent T. A more commonly used range is from 4 to 8 percent.

The separating gel solutions were dispensed in a rectangular mold (slab) or in a tube, a layer of water was placed on the surface to avoid a meniscus forming on the gel surface and the gels were allowed to solidify. In some cases, after the separating gels solidified and the liquid layer was removed, an acrylamide stacking gel mixture of about 3.0 percent T, made with the same buffer at about neutral pH was prepared and dispensed on top of the separating gel in the gel tube or slab and allowed to polymerize. A layer of water was placed over the stacking gel to provide a flat surface. The exact monomer concentration of the stacking gel is not important.

Isoenzymes can be measured in tissue extracts, serum and other body fluids. Tissue extracts can be prepared by homogenizing the specimen in a four-fold volume of 12 percent sucrose or in a buffer in an ice bath,. The supernatant obtained is used. Serum samples or other body fluids can be obtained and used immediately or stored at −20° C.

The liquid layer on top of the gel was removed, and a sample mixture containing the LDH or CK isoenzymes (sometimes with tracking dye) was placed on top of the stacking gel or directly on top of the separating gel. The electrolyte buffer, 2-amino-2-methyl-1,3-propanediol tuarine at a pH of between 8 to 10, was then placed so that both ends of the gel were in contact with the electrolyte buffer. The samples were then subjected to electrophoresis at a constant current of about 2 to 5 milliamps per sample and the electrophoresis allowed to proceed for a specified period of time or until the tracking dye had reached approximately the bottom of the gel. The gels were removed from the electrophoresis apparatus, and placed in an appropriate staining solution which includes a stain and a substrate which is capable of being reacted upon by an isoenzyme, to enable identification of isoenzymes.

For example, if the isoenzyme to be tested for is LDH, the staining mixture can include a stain, such as a tetrazolium salt, phenazine methosulfate, and as the enzyme substrate, lactate and NAD. Reduction of NAD will oxidize a tetrazolium salt to a colored formazan and locate the isoenzymes as colored bands [See Clin. Biochem., 7:29 (1974); Am. J. of Clin. Path., 43(3): 256 (1965)].

If the isoenzyme to be tested for is CK, the staining procedure can be based (among many) on a spectrophotometric procedure utilizing Kornberg's assay for ATP. The staining mixture can contain glucose, ADP, adenosine monophosphate (AMP), nicotinamide adenine dinucleotide phosphate (NADP), hexokinase, glucose-6-phosphate dehydrogenase, and as a substrate which is acted upon by the CK isoenzyme, creatine phosphate (CP).

The analysis involves the following stepwise equations [See Clinica Chemica Acta, 21:151 (1969)]

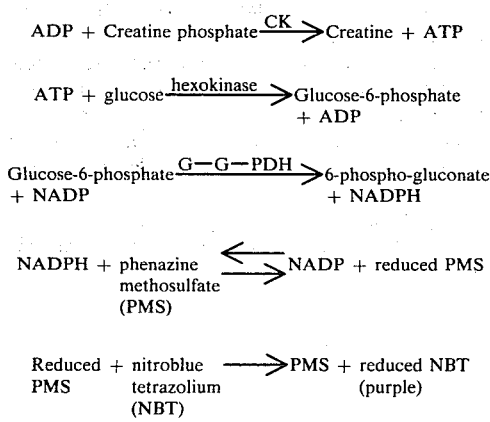

or alternatively the fluorescence of NADPH can be measured after reaction 3.

The above are some examples of LDH and CK staining procedures. However, there are numerous other methods for the staining of isoenzymes, which are known and can be utilized.

The gels that are to be stored for use at another time are stored in a storage buffer of similar composition to the gel buffer to prevent drying out of the gels and usually containing some preservative to prevent bacterial growth.

EXAMPLE I

A. Preparation of Separating Gel

A 0.3 M solution of ammediol chloride buffer at a pH of 6.7 to 6.9 was prepared by mixing together ammediol with hydrochloric acid. This solution also contained approximately 300 μl N,N,N',N'-tetramethylethylenediamine per 100 ml of solution. This solution was mixed with an aqueous solution of acrylamide gel and N,N'-methylenebisacrylamide (Bis), ammonium persulfate and water. The acrylamide-Bis mixture was prepared by adding 38.9 g acrylamide and 1.1 g Bis to 100 ml $H_2O$. The catalyst solution was prepared by adding 140 mg of ammonium persulfate in 100 ml $H_2O$. The above components were mixed in a ratio of 2:1:2.5:2.5 to obtain a 5 percent gel. A 75 mm gel tube was filled to about 50 mm height with the mixture and allowed to solidify. No stacking gel was poured.

B. Preparation of Electrolyte Buffer

The electrolyte buffer was prepared by mixing ammediol with taurine to produce a buffer of about 0.01 M ammediol and 0.04 M taurine at a pH of approximately 8.5.

C. Preparation of Samples

Serum samples were diluted 1:5 with a sucrose solution of 10.6 gm of a mixture of 94 percent (w/w) sucrose and 6 percent (w/w) tris (hydroxymethyl) aminomethane to which 20 ml of water was added.

The electrophoresis was run at about 3 milliamps per gel for about 70 minutes. The gels were then taken out of the tubes, and stained.

For LDH testing, the stain mixture contained a stain and as a substrate which is capable of being acted upon by LDH isoenzymes, sodium lactate. The stain mixture of this example was prepared by mixing 8 parts of solution A and 1 part of solution B and adjusting the pH to 8.6. Solution A contains 0.15 M potassium phosphate monobasic, 0.13 M sodium lactate, 0.012 M sodium chloride, 0.28 mM magnesium chloride and 0.35 mM nitro-blue tetrazolium. Solution B contains 6.9 mM nicotinamide adenine dinucleotide and 0.7 mM phenazine methosulfate. The pH of the mixture is adjusted to 8.6 with sodium hydroxide.

The gels were placed in contact with the stain mixture for 20 minutes and then placed in a 7 percent acetic acid mixture to stop the color reaction and for preservation of the developed gels. The stained bands were quantitated in a densitometer at 570 nm wavelength.

The gels were examined and it was determined that 5 bands were present, indicating the successful separation of LDH isoenzymes into $LDH_1$-$LDH_5$. Good resolution was obtained; the bands were sharp and clear and had very low interfering background.

EXAMPLE II

A. Preparation of Separating and Stacking Gels

Separating gels were prepared with ammediol sulfate and solidified as described in Example I with a pH of 6.4 to 7.3.

A stacking gel was prepared by mixing the above buffer, H₂O, ammonium persulfate (0.2 percent) and acrylamide—Bis solution (12.5 percent T, 20 percent C) in equal proportions. One hundred µl of this solution was placed over the separating gel and allowed to polymerize. The stacking gel was left out in many runs.

B. Preparation of Electrolyte Buffer

The electrolyte buffer was prepared by mixing ammediol with taurine to produce a buffer of about 0.02 M ammediol and 0.05 M taurine at a pH of about 8 to 10.

C. Preparation of Samples

Serum samples were diluted 1:10 with the sucrosetris solution of Example I and also with a sucroseammediol solution of similar concentration.

The electrophoresis was run at about 4 milliamps per gel for about 50 minutes. The gels were then taken out of the tubes, stained and fixed.

For LDH testing, the stain mixture contained a stain and a substrate which is capable of being acted upon by LDH isoenzymes. The mixture used in this example was prepared by mixing the following solutions: lactic acid in 0.05 M tris pH 8.6, 6.1 mM nicotinamide adenine dinucleotide in the same tris buffer, diaphorase (100 U/mg) 1 mg per ml of H₂O and p-iodonitrotetrazolium violet (INT) 2.5 mg per ml of H₂O containing 0.4 percent Triton X-100. The above solutions were mixed in the ratio 9:1:1:1.

The gels were placed in contact with the stain mixture for 30 minutes and then placed in a 7 percent acetic acid mixture to stop the color reaction and for preservation of the developed gels. The stained bands were quantitated in a densitometer at 500 nm wavelength.

The gels were examined and it was determined that 5 bands were present, indicating the successful separation of LDH isoenzymes into $LDH_1$–$LDH_5$. Good resolution was obtained; the bands were sharp and clear and had very low interfering background.

EXAMPLE III

A. Preparation of Separating Gel

A separating gel was prepared as described in Example I with a 0.15 M solution of ammediol chloride, pH 6.6 to 7.1.

No stacking gel was prepared.

B. Preparation of Electrolyte Buffer

The electrolyte buffer was prepared as described in Example I, using 0.01 M ammediol and 0.04 M taurine at a pH of about 8 to 10.

C. Preparation of Samples

Serum samples were diluted 1:5 with a sucrose solution as described in Example I.

The electrophoresis was run at about 3 milliamps per gel for about 70 minutes. The gels were then taken out of the tubes and stained for one hour.

For CK testing, the stain mixture contained a stain and a substrate which is capable of being acted upon by CK isoenzymes. The mixture used in this example had approximately the following composition: 52 mM creatine phosphate, 2 mM adenoside diphosphate, 9 mM magnesium aspartate, 6 mM adenosine monophasphate, 2 mM nicotinamide adenine dinucleotide phosphate, 19 mM glucose, 28 mM glutathione, $3 \times 10^3$ IU/liter hexokinase, $1 \times 10^3$ IU/liter glucose-6-phosphate dehydrogenase, buffer (pH $6.8 \pm 0.1$).

The fluorescence of the bands was quantitated using a Transidyne densitometer, Transidyne General Corporation, Ann Arbor, Mich. 48106, using the fluorescent mode.

It was determined that three CK isoenzymes bands were present, corresponding to MM, MB and BB. Good resolution was obtained; the bands were sharp and clear and had very low interfering background.

What is claimed is:

1. A method for separating isoenzymes which comprises the steps of applying an isoenzyme-containing sample to a support medium of polyacryl-amide gel containing acrylamide monomers in a buffer solution of a salt of 2-amino-2-methyl-1,3-propanediol at a pH of about 6.4 to 7.3 and an electrolyte buffer of 2-amino-2-methyl-1,3-propanediol taurine at a pH of about 8.0 to 10.0, subjecting the mixture to a differential electrical potential to produce migration of the isoenzymes and buffer ions and determining the presence of separated isoenzymes.

2. A method as claimed in claim 1 wherein the 2-amino-2-methyl-1,3-propanediol has a pH of about 6.8 to 7.1.

3. A method as claimed in claim 1 wherein the gel buffer is selected from the group consisting of 2-amino-2-methyl-1,3-propanediol chloride, sulfate, nitrite and fluoride.

4. A method as claimed in claim 3 wherein the gel buffer is 2-amino-2-methyl-1,3-propanediol chloride or sulfate.

5. A method as claimed in claim 1 wherein the sample is serum or a tissue extract.

6. A method as claimed in claim 1 wherein the isoenzymes are lactate dehydrogenase and creatine kinase.

7. A method as claimed in claim 1 wherein the presence of separated isoenzymes is determined by staining the gel in the presence of a stain and a substrate which is acted upon by isoenzymes present, whereby separated isoenzyme bands are produced, terminating said enzymatic reaction, and determining the presence of said isoenzymes.

* * * * *